(12) United States Patent
Joseph et al.

(10) Patent No.: US 12,186,014 B2
(45) Date of Patent: *Jan. 7, 2025

(54) MONOPOLAR RETURN PAD INCLUDING A PATHWAY FOR EVACUATING SURGICAL SMOKE

(71) Applicant: Covidien LP, Mansfield, MA (US)

(72) Inventors: Daniel A. Joseph, Golden, CO (US); Tony Moua, Broomfield, CO (US)

(73) Assignee: Covidien LP, Mansfield, MA (US)

( * ) Notice: Subject to any disclaimer, the term of this patent is extended or adjusted under 35 U.S.C. 154(b) by 182 days.

This patent is subject to a terminal disclaimer.

(21) Appl. No.: 17/831,681

(22) Filed: Jun. 3, 2022

(65) Prior Publication Data

US 2022/0287771 A1 Sep. 15, 2022

Related U.S. Application Data

(63) Continuation of application No. 16/711,603, filed on Dec. 12, 2019, now Pat. No. 11,364,076.

(51) Int. Cl.
*A61B 18/16* (2006.01)
*A61B 18/12* (2006.01)
(Continued)

(52) U.S. Cl.
CPC .......... *A61B 18/16* (2013.01); *A61B 18/1206* (2013.01); *A61B 2017/00477* (2013.01); *A61B 2017/00951* (2013.01); *A61B 2018/00077* (2013.01); *A61B 2018/00577* (2013.01); *A61B 2018/00589* (2013.01); *A61B 2018/00601* (2013.01); *A61B 2018/1253* (2013.01); *A61B 2018/126* (2013.01);
(Continued)

(58) Field of Classification Search
CPC ............... A61B 18/1206; A61B 18/16; A61B 2018/00077; A61B 2018/00577; A61B 2018/00589; A61B 2018/00601; A61B 2018/1253; A61B 2018/126; A61B 2018/1467; A61B 2018/167; A61B 2218/008; A61B 2017/00477; A61B 2017/00951

See application file for complete search history.

(56) References Cited

U.S. PATENT DOCUMENTS 3,122,171 A 2/1964 Britton et al.
3,720,209 A 3/1973 Bolduc
(Continued)

FOREIGN PATENT DOCUMENTS

CA 1219642 A1 3/1987
DE 3206947 A1 9/1983
(Continued)

OTHER PUBLICATIONS

Boyles, Walt; "Instrumentation Reference Book", 2002; Butterworth-Heinemann ; 262-264.
(Continued)

*Primary Examiner* — Khadijeh A Vahdat
(74) *Attorney, Agent, or Firm* — Carter, DeLuca & Farrell LLP (57) ABSTRACT

A combination patient return pad and surgical smoke evacuator includes a return electrode configured to attach to a surface and a suction tube for drawing surgical smoke from a surgical site.

19 Claims, 7 Drawing Sheets

(51) Int. Cl.
  *A61B 17/00* (2006.01)
  *A61B 18/00* (2006.01)
  *A61B 18/14* (2006.01)

(52) U.S. Cl.
  CPC . *A61B 2018/1467* (2013.01); *A61B 2018/167* (2013.01); *A61B 2218/008* (2013.01)

(56) References Cited

U.S. PATENT DOCUMENTS

| | | | |
|---|---|---|---|
| 3,913,583 A | 10/1975 | Bross | |
| 3,923,063 A | 12/1975 | Andrews et al. | |
| 4,126,137 A | 11/1978 | Archibald | |
| 4,166,465 A | 9/1979 | Esty et al. | |
| 4,188,927 A | 2/1980 | Harris | |
| 4,200,104 A | 4/1980 | Harris | |
| 4,267,840 A * | 5/1981 | Lazar | A61B 18/16 607/152 |
| 4,303,073 A | 12/1981 | Archibald | |
| 4,304,235 A | 12/1981 | Kaufman | |
| 4,387,714 A | 6/1983 | Geddes et al. | |
| 4,494,541 A | 1/1985 | Archibald | |
| 4,669,468 A | 6/1987 | Cartmell et al. | |
| 4,788,977 A | 12/1988 | Farin et al. | |
| 4,799,480 A | 1/1989 | Abraham et al. | |
| 4,844,063 A | 7/1989 | Clark | |
| 4,942,313 A | 7/1990 | Kinzel | |
| 5,015,243 A | 5/1991 | Schifano | |
| 5,042,981 A | 8/1991 | Gross | |
| 5,087,257 A | 2/1992 | Farin et al. | |
| 5,246,439 A | 9/1993 | Hebborn et al. | |
| 5,312,401 A | 5/1994 | Newton et al. | |
| 5,370,645 A | 12/1994 | Klicek et al. | |
| 5,452,725 A | 9/1995 | Martenson | |
| 5,678,545 A | 10/1997 | Stratbucker | |
| 5,688,269 A | 11/1997 | Newton et al. | |
| 5,695,494 A | 12/1997 | Becker | |
| 5,720,744 A | 2/1998 | Eggleston et al. | |
| 5,830,212 A | 11/1998 | Cartmell et al. | |
| 5,836,942 A | 11/1998 | Netherly et al. | |
| 5,868,742 A | 2/1999 | Manes et al. | |
| 5,947,961 A | 9/1999 | Netherly | |
| 5,971,981 A | 10/1999 | Hill et al. | |
| 6,007,532 A | 12/1999 | Netherly | |
| 6,053,910 A | 4/2000 | Fleenor | |
| 6,083,221 A | 7/2000 | Fleenor et al. | |
| 6,171,304 B1 | 1/2001 | Netherly et al. | |
| 6,214,000 B1 | 4/2001 | Fleenor et al. | |
| 6,258,085 B1 | 7/2001 | Eggleston | |
| 6,310,611 B1 | 10/2001 | Caldwell | |
| 6,413,255 B1 | 7/2002 | Stern | |
| 6,454,764 B1 | 9/2002 | Fleenor et al. | |
| 6,544,258 B2 | 4/2003 | Fleenor et al. | |
| 6,582,424 B2 | 6/2003 | Fleenor et al. | |
| 6,666,859 B1 | 12/2003 | Fleenor et al. | |
| 6,860,881 B2 | 3/2005 | Sturm et al. | |
| 6,891,488 B1 | 5/2005 | McDaniel et al. | |
| 6,942,650 B1 * | 9/2005 | Schultz | B01D 46/24 604/315 |
| 7,160,293 B2 | 1/2007 | Sturm et al. | |
| 7,166,102 B2 | 1/2007 | Fleenor et al. | |
| 7,169,145 B2 | 1/2007 | Isaacson et al. | |
| 7,267,675 B2 | 9/2007 | Stern et al. | |
| 7,422,589 B2 | 9/2008 | Newton et al. | |
| 7,699,395 B1 | 4/2010 | Bozarth et al. | |
| 8,187,263 B2 | 5/2012 | Behnke et al. | |
| 8,298,225 B2 | 10/2012 | Gilbert | |
| 8,342,459 B2 | 1/2013 | Garrison et al. | |
| 8,523,853 B2 | 9/2013 | Dunning | |
| 9,987,072 B2 | 6/2018 | McPherson | |
| 10,010,693 B2 | 7/2018 | Sims | |
| 11,364,076 B2 | 6/2022 | Joseph et al. | |

| | | | |
|---|---|---|---|
| 2001/0029367 A1 * | 10/2001 | Fleenor | A61B 50/13 607/152 |
| 2003/0065320 A1 | 4/2003 | Wellman | |
| 2003/0139741 A1 | 7/2003 | Goble et al. | |
| 2005/0085806 A1 | 4/2005 | Auge et al. | |
| 2006/0041251 A1 | 2/2006 | Odell et al. | |
| 2006/0041252 A1 | 2/2006 | Odell et al. | |
| 2006/0074411 A1 | 4/2006 | Carmel et al. | |
| 2007/0049916 A1 | 3/2007 | Isaacson et al. | |
| 2007/0073284 A1 | 3/2007 | Sturm et al. | |
| 2007/0167942 A1 | 7/2007 | Rick | |
| 2007/0244478 A1 | 10/2007 | Bahney | |
| 2008/0047064 A1 | 2/2008 | Theran | |
| 2008/0281309 A1 | 11/2008 | Dunning et al. | |
| 2008/0281310 A1 | 11/2008 | Dunning et al. | |
| 2008/0281311 A1 | 11/2008 | Dunning et al. | |
| 2009/0234352 A1 | 9/2009 | Behnke et al. | |
| 2013/0006236 A1 | 1/2013 | Greep et al. | |
| 2014/0343548 A1 * | 11/2014 | Benn | A61B 18/1402 606/41 |
| 2017/0360499 A1 | 12/2017 | Greep et al. | |
| 2018/0206905 A1 | 7/2018 | Batchelor et al. | |
| 2019/0159825 A1 | 5/2019 | Frampton et al. | |
| 2019/0298444 A1 * | 10/2019 | Xu | A61B 1/04 |

FOREIGN PATENT DOCUMENTS

| | | |
|---|---|---|
| DE | 3544443 A1 | 6/1987 |
| DE | 4238263 A1 | 5/1993 |
| DE | 4231236 A1 | 3/1994 |
| DE | 19717411 A1 | 11/1998 |
| DE | 19801173 C1 | 7/1999 |
| DE | 10328514 B3 | 3/2005 |
| DE | 102004010940 A1 | 9/2005 |
| EP | 0262888 A2 | 4/1988 |
| EP | 0390937 A1 | 10/1990 |
| EP | 0836868 A2 | 4/1998 |
| EP | 0930048 A2 | 7/1999 |
| EP | 1051949 A1 | 11/2000 |
| EP | 1076350 A2 | 2/2001 |
| EP | 1468653 A2 | 10/2004 |
| EP | 1645236 A1 | 4/2006 |
| EP | 1707151 A2 | 10/2006 |
| EP | 1808144 A2 | 7/2007 |
| EP | 1902684 A1 | 3/2008 |
| FR | 2276027 A1 | 1/1976 |
| FR | 2516782 A1 | 5/1983 |
| GB | 2054382 A | 2/1981 |
| GB | 2374532 A | 10/2002 |
| WO | 9737719 A1 | 10/1997 |
| WO | 9818395 A1 | 5/1998 |
| WO | 9909899 A1 | 3/1999 |
| WO | 9911187 A1 | 3/1999 |
| WO | 0028908 A1 | 5/2000 |
| WO | 0032122 A1 | 6/2000 |
| WO | 0053113 A1 | 9/2000 |
| WO | 0065993 A1 | 11/2000 |
| WO | 0187175 A1 | 11/2001 |
| WO | 02058579 A1 | 8/2002 |
| WO | 02060526 A1 | 8/2002 |
| WO | 03094766 A2 | 11/2003 |
| WO | 2004028385 A1 | 4/2004 |
| WO | 2005087124 A1 | 9/2005 |
| WO | 2005099606 A1 | 10/2005 |
| WO | 2005115262 A1 | 12/2005 |
| WO | 2008009385 A1 | 1/2008 |

OTHER PUBLICATIONS

Partial European Search Report dated Apr. 14, 2021, issued in corresponding EP Appln. No. 20212152, 10 pages.
3 European Search Report dated Jul. 15, 2021, issued in corresponding EP Appln. No. 20212152, 9 pages.

* cited by examiner

MONOPOLAR RETURN PAD INCLUDING A PATHWAY FOR EVACUATING SURGICAL SMOKE

CROSS-REFERENCE TO RELATED APPLICATION

This application is a Continuation Application of U.S. patent application Ser. No. 16/711,603, filed on Dec. 12, 2019, now U.S. Pat. No. 11,364,076 the entire contents of which being incorporated by reference herein.

INTRODUCTION

The present disclosure relates generally to electrosurgical systems and methods. More particularly, the present disclosure is directed to a monopolar return pad having a pathway for evacuating surgical smoke.

BACKGROUND

Energy-based tissue treatment is well-known in the art. Various types of energy (such as electrical, ultrasonic, microwave, cryogenic, heat, laser, and/or the like) are applied to tissue to achieve a desired result. Electrosurgery involves application of high radio frequency electrical current to a surgical site to cut, ablate, coagulate, seal or otherwise treat tissue. Energy-based surgical devices typically include an isolation boundary between the patient and the energy source.

In monopolar electrosurgery, the active electrode is typically part of the surgical instrument held by the surgeon and applied to the tissue to be treated. One or more patient return electrodes are placed remotely from the active electrode to carry the current back to the generator and disperse current applied by the active electrode.

SUMMARY

In accordance with aspects of the disclosure, a patient return pad is provided and includes a sheet having a bottom surface, a return electrode coupled to the bottom surface of the sheet and configured to receive electrosurgical energy from an active electrode, and a suction tube configured to be coupled to the sheet for vacuuming surgical smoke.

In aspects, the bottom surface of the sheet may include an interior section and an outer peripheral section at least partially surrounding the interior section. The return electrode may be coupled to the outer peripheral section of the bottom surface.

In aspects, the suction tube may have an end portion attached to the sheet and may define an opening in communication with the interior section of the sheet.

In aspects, the interior section may be recessed relative to the outer peripheral section, such that the bottom surface of the sheet defines a cavity therein. The opening of the end portion may be in fluid communication with the cavity.

In aspects, the patient return pad may further include a foam pad received in the cavity.

In aspects, the bottom surface of the sheet may be configured to form a cavity between the interior section of the bottom surface and a tissue surface upon attaching the outer peripheral section of the bottom surface to the tissue surface.

In aspects, the patient return pad may further include a conductive adhesive disposed on the outer peripheral section.

In aspects, the sheet may have a front end and a rear end and may define a vacuum path from the front end toward the rear end. The suction tube may be coupled to the rear end.

In aspects, the patient return pad may further include a return lead having a first end portion coupled to the return electrode and a second end portion configured to electrically couple the return electrode to an electrosurgical energy source.

In aspects, the return lead may extend through or over the suction tube.

In accordance with another aspect of the disclosure, a combination patient return pad and surgical smoke evacuator is provided and includes a housing and a return electrode. The housing defines a cavity therein configured to receive suction. The return electrode is coupled to a bottom surface of the housing. The return electrode has an adherent and conductive bottom surface configured to receive electrosurgical energy from an active electrode.

In aspects, the combination patient return pad and surgical smoke evacuator may further include a suction tube. The suction tube may have a first end portion configured to be coupled to a vacuum source and a second end portion coupled to the housing and in fluid communication with the cavity for vacuuming surgical smoke through the cavity.

In aspects, the combination patient return pad and surgical smoke evacuator may further include a foam pad received in the cavity.

In aspects, the housing may have an opened front end and a rear end and may define a vacuum path from the front end toward the rear end.

In aspects, the combination patient return pad and surgical smoke evacuator may further include a return lead having a first end portion coupled to the return electrode and a second end portion configured to electrically couple the return electrode to an electrosurgical energy source.

Further details and aspects of exemplary embodiments of the disclosure are described in more detail below with reference to the appended figures. Any of the above aspects and embodiments of the disclosure may be combined without departing from the scope of the disclosure.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

BRIEF DESCRIPTION OF THE DRAWINGS

The above and other aspects, features, and advantages of the present disclosure will become more apparent in light of the following detailed description when taken in conjunction with the accompanying drawings, in which.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

A combination patient return pad and surgical smoke evacuator is provided and includes a sheet of material configured to be positioned on a surface adjacent a surgical site, a return electrode formed with or otherwise coupled to the sheet of material, and a suction tube coupled to the sheet of material. The return electrode receives electrosurgical energy from an active electrode and the suction tube removes surgical smoke from the surgical site.

Figure 1:
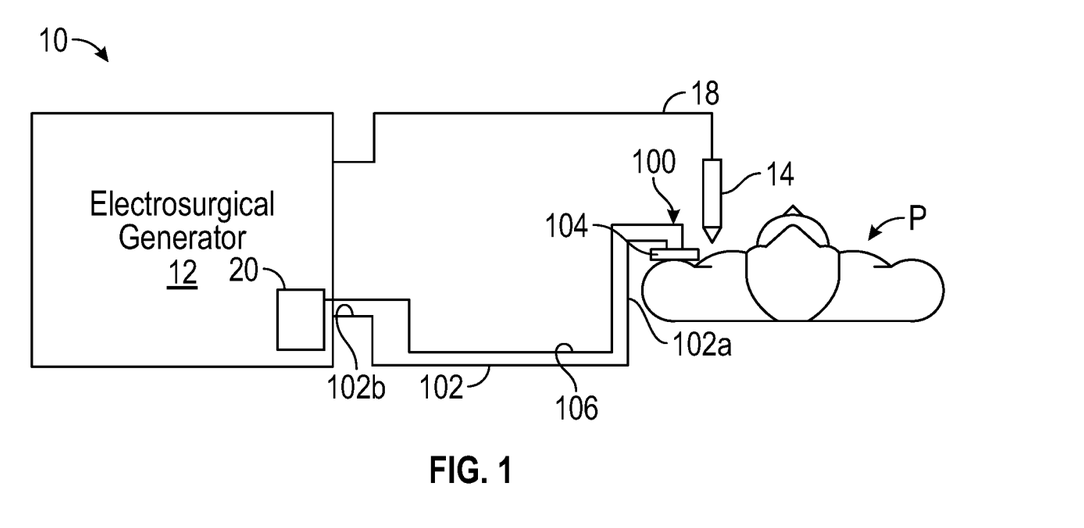
FIG. 1 is a schematic illustration of a monopolar electrosurgical system including an electrosurgical generator, an electrosurgical instrument, and a patient return pad.

FIG. 1 illustrates an electrosurgical system 10 including an electrosurgical energy source, such as, for example, an electrosurgical generator 12, an electrosurgical instrument 14 coupled to the generator 12, and a patient return pad 100 coupled to the generator 12 via a return cable 102. The electrosurgical generator 12 may be any suitable type of generator and may include a plurality of connectors to accommodate various types of electrosurgical instruments (e.g., monopolar, bipolar, and/or the like). The electrosurgical generator 12 may also include a vacuum source 20 for drawing surgical smoke from a surgical site. In aspects, the vacuum source 20 and electrosurgical generator 12 may be separate components.

The electrosurgical instrument 14 has one or more active electrodes (not explicitly shown) for treating tissue of a patient P. The instrument 14 may be a monopolar instrument including one or more active electrodes (such as, for example, an electrosurgical cutting probe, ablation electrode(s), and/or the like). Electrosurgical RF energy is supplied to the instrument 14 by the generator 12 via an active electrosurgical cable 18, which is connected to an active output terminal, allowing the instrument 14 to coagulate, ablate and/or otherwise treat tissue.

Figure 2:
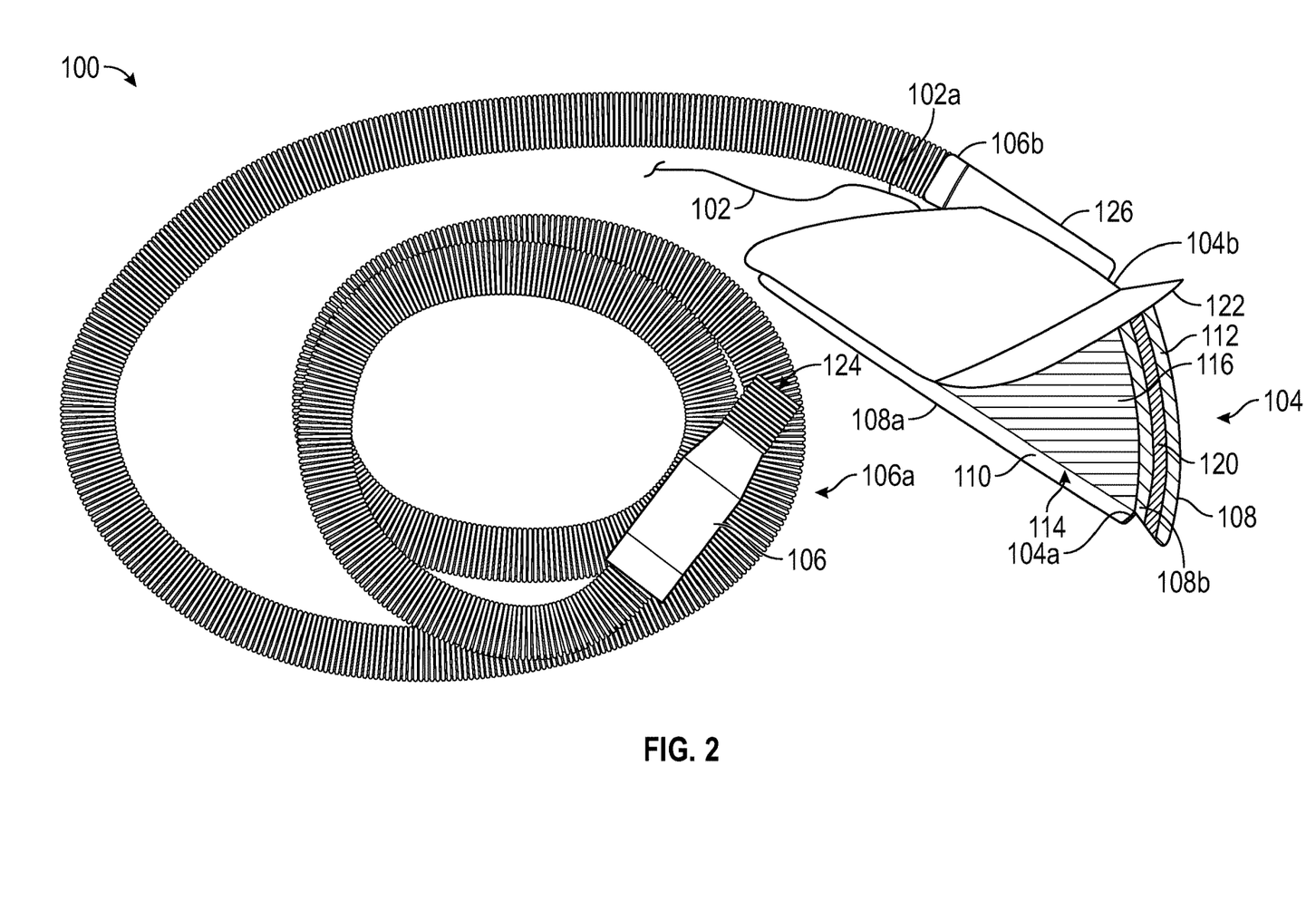
FIG. 2 is a perspective view illustrating the patient return pad of FIG. 1.
Figure 3:
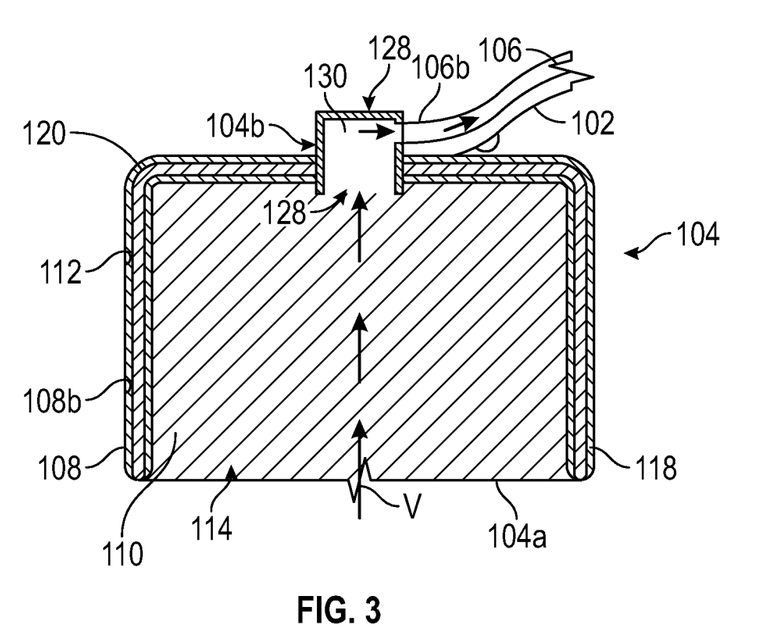
FIG. 3 is a partial bottom view of the patient return pad of FIG. 1.

With reference to FIGS. 1-3, the patient return pad 100 is a combination patient return pad and smoke evacuator and generally includes a head 104, the return cable 102, and a suction tube 106 supported by the head 104. The head 104 may have a square shape, a triangular shape, or any other suitable shape. The head 104 has an opened front end 104a and an opened rear end 104b. A vacuum pathway V is defined between the front 104a and rear ends 104b of the head 104 and extends in the direction toward the rear end 104b.

The head 104 includes a pliable sheet 108 or surface, such as, for example, fabric, plastic, or any other suitable material to facilitate return pad operation. The pliable sheet 108 of the head 104 has a top surface 108a, and a bottom surface 108b configured to face and attach to a tissue surface of a patient located adjacent a surgical site. The bottom surface 108b of the pliable sheet 108 has an interior section 110 and an outer peripheral section 112 partially surrounding the interior section 110. The interior section 110 may be recessed relative to the outer peripheral section 112 to define a cavity 114. As such, upon attaching the outer peripheral section 112 of the bottom surface 108b to a tissue surface (e.g., skin of a patient), the interior section 110 of the bottom surface 108b is elevated above the tissue surface to allow air (e.g., surgical smoke) to pass from the opened front end 104a of the head 104 to the opened rear end 104b of the head 104.

In aspects, the head 104 may include a pad 116, such as, for example, a foam pad, received in the cavity 114 to assist in maintaining the cavity 114 open when the bottom surface 108b is attached to a surface. In aspects, the pad 116 may be fabricated from any suitable material and may be conductive or non-conductive. The pad 116 may be coated with an adherent film, such as, for example, polyethylene. The outer peripheral section 112 of the bottom surface 108b of the pliable sheet 108 has an electrically-conductive adhesive coating 118 (FIG. 3) disposed thereon. In aspects, the adhesive 118 may be a liquid, a gel, a film, or the like.

The head 104 includes a return electrode 120 attached to the outer peripheral section 112 of the bottom surface 108b and may have the same shape as the outer peripheral section 112 or may extend over the outer peripheral section 112 and the entire bottom surface of the pad 116. In some aspects, the pad 116 may be fabricated from a conductive material so as to act as the return electrode. The return electrode 120 may be a sheet, a wire, or a coating and may be made from materials that include aluminum, copper, mylar, metalized mylar or other suitable conductive material. The return electrode 120 may also include an insulator, glue, a conductive adhesive, gel or other material that is configured to attach the return electrode 120 to tissue and/or to facilitate the transfer of electrosurgical energy to the patient's skin. It is contemplated that the return electrode 120 and the outer peripheral section 112 have a sufficient surface area to conduct electrosurgical energy to the patient's skin without causing damage to the skin. The head 104 may further include a backing 122 (FIG. 2) that covers the bottom surface 108b of the pliable sheet 108. The backing 122 may be selectively removed (e.g., peeled) from the bottom surface 108b to expose the adhesive 118.

The return electrode 120 has the return lead 102 extending therefrom. In particular, the return lead 102, which may be a wire or a cable, has a first end portion 102a attached to the return electrode 120, and a second end portion 102b (FIG. 1) attached to the electrosurgical generator 12. The return lead 102 transfers electrosurgical energy received by the return electrode 120 to the electrosurgical generator 12.

The suction tube 106 of the patient return pad 100 has a first end portion 106a configured to be coupled to the vacuum source 20 (FIG. 1) and a second end portion 106b configured to be either permanently coupled or detachably coupled to the rear end 104b of the head 104. The suction tube 106 defines a longitudinal channel 124 therethrough to allow for the passage of surgical smoke. The second end portion 106b of the suction tube 106 may have a connector 126 attached thereto that couples the suction tube 106 to the head 104. In aspects, the second end portion 106b of the suction tube 106 may be received in the rear end 104b of the head 104. The connector 126 extends through the open rear end 104b of the head 104 and defines an opening 128 in fluid communication with the cavity 114, such that surgical smoke may pass from the cavity 114 and into the suction tube 106 via the opening 128. The connector 126 may have a flat bottom surface 130 that is coplanar with the outer peripheral section 112 of the bottom surface 108b of the pliable sheet 108 to prevent air gaps from forming between the bottom surface 108b and a tissue surface. The return lead 102 may extend through the channel 124 of the suction tube 106, around the suction tube 106, or run alongside of and separate from the suction tube 106.

During an electrosurgical procedure, the backing 122 of the head 104 of the patient return pad 100 is removed and the bottom surface 108b of the pliable sheet 108 of the head 104 is placed at a location adjacent the surgical site and in contact with tissue of a patient P (e.g., skin). In aspects where only the vacuum function of the head 104 is desired, the bottom surface 108b of the pliable sheet 108 may be placed on a surgical drape or other suitable surface adjacent the surgical site. The adhesive 118 on the outer peripheral section 112 of the bottom surface 108b fixes the outer peripheral section 112 to the patient's skin. The pad 116 of the head 104 also contacts the skin surface, whereby the interior section 110 is maintained in spaced relation from the skin surface and the front end 104a of the head 104 is maintained in an opened state. Due to the return electrode 120 being attached to the outer peripheral section 112, the return electrode 120 is placed in contact with or otherwise electrically connected to the skin via the adhesive 118 (e.g., conductive adhesive).

The monopolar electrode of the surgical instrument 14 may be activated to treat tissue. During treatment, the electrosurgical energy passes from the generator 12, through the electrosurgical instrument 14 and into the patient P to treat the tissue. The electrosurgical energy then travels from the tissue back to the electrosurgical generator 12 via the return electrode 120 in the patient return pad 100. During the procedure, the vacuum source 20 may be activated to clear any smoke or debris from the surgical field while the foam pad 116 prevents debris from entering the cavity 114. In aspects, the vacuum source 20 may be activated prior to treating tissue and the generation of smoke. Upon activating the vacuum source 20, a suction pathway is generated and carries the surgical smoke from the surgical field and into the cavity 114 via the front end 104a of the head 104. The surgical smoke passes into the suction tube 106 via the opening 128 in the connector 126. In this way, the patient return pad 100 functions both as a return electrode for receiving electrosurgical energy from the active electrode and as a surgical smoke evacuator. The vacuum source 20 may remain on for a selected period of time after activation of the generator 12 has ceased.

Figure 4:
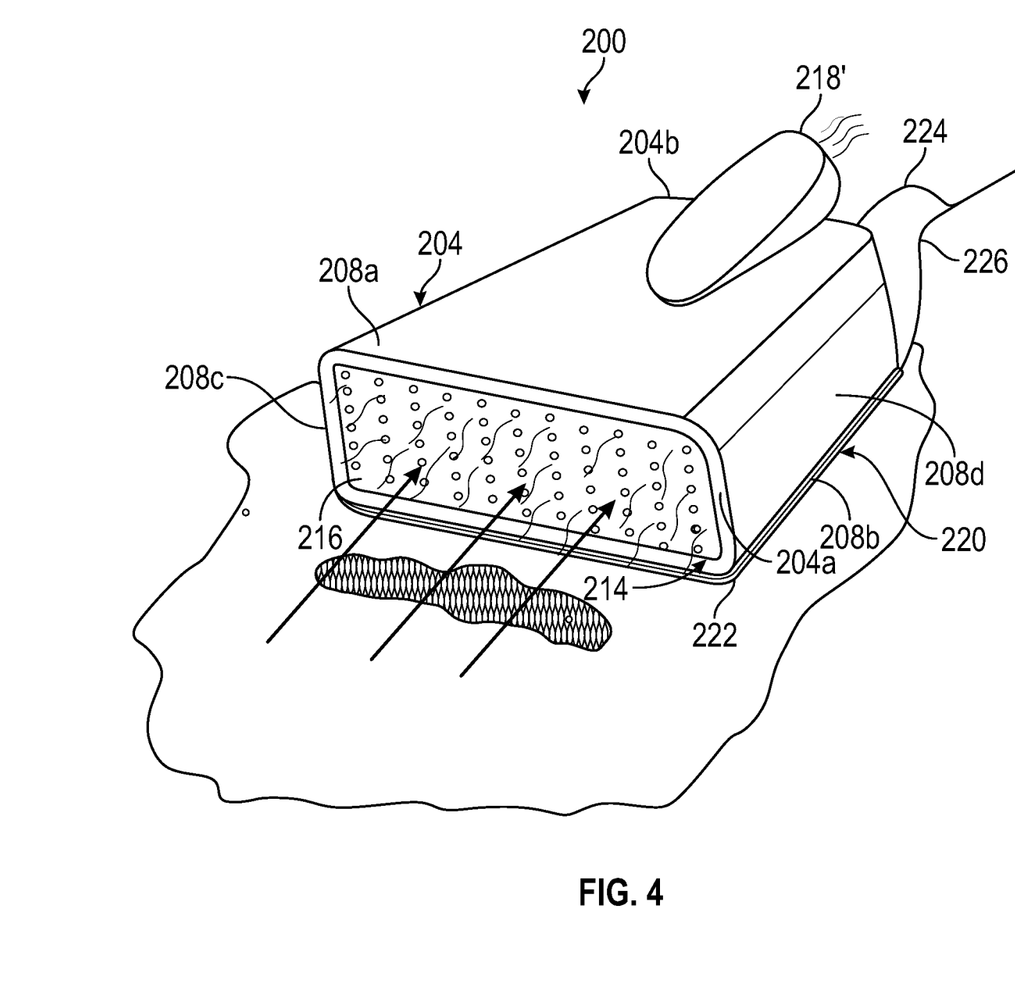
FIG. 4 is a perspective view illustrating another embodiment of a patient return pad for use in the monopolar electrosurgical system.
Figure 5:
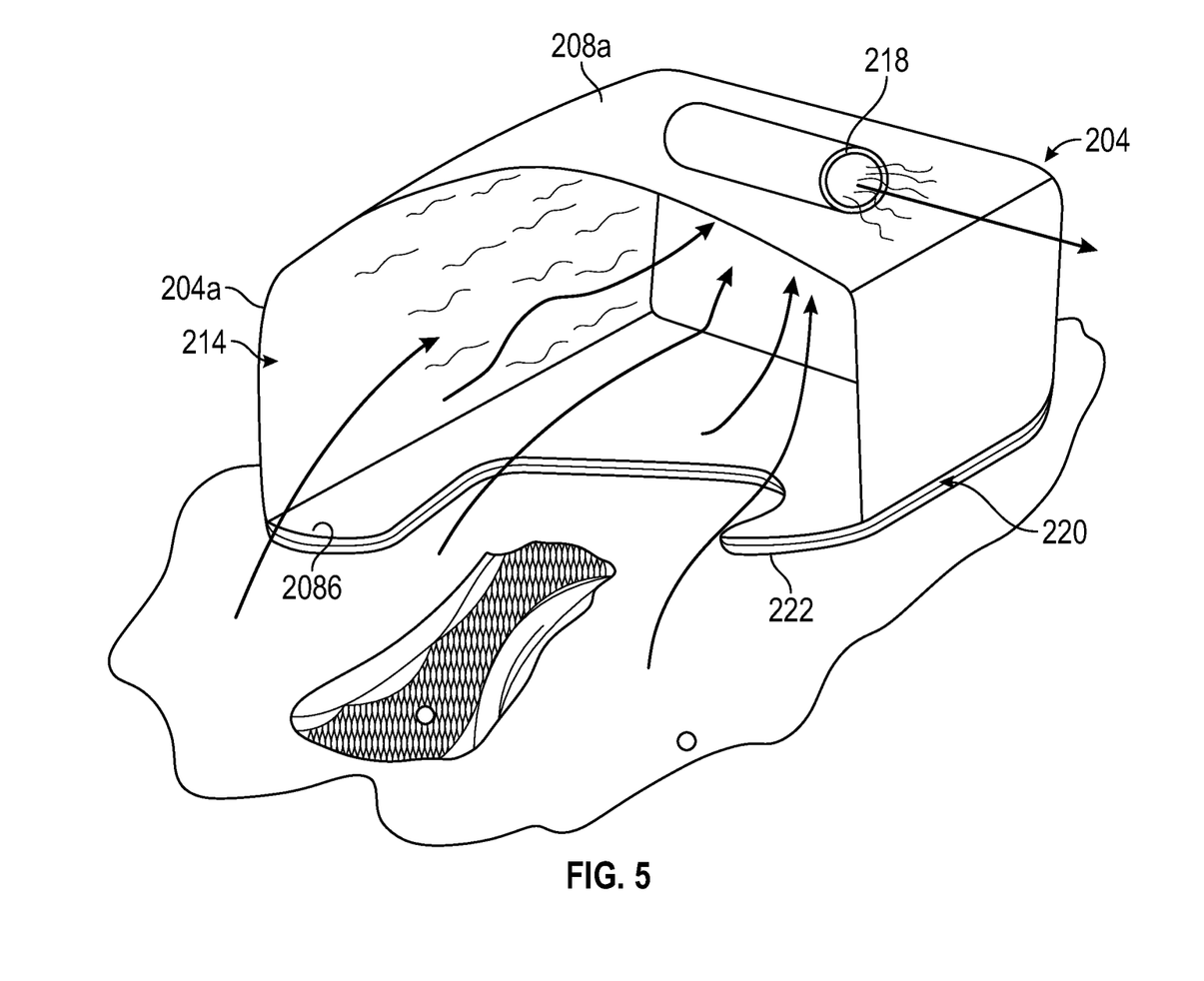
FIG. 5 is a front, perspective view illustrating a patient return pad with a foam pad removed.
Figure 6:
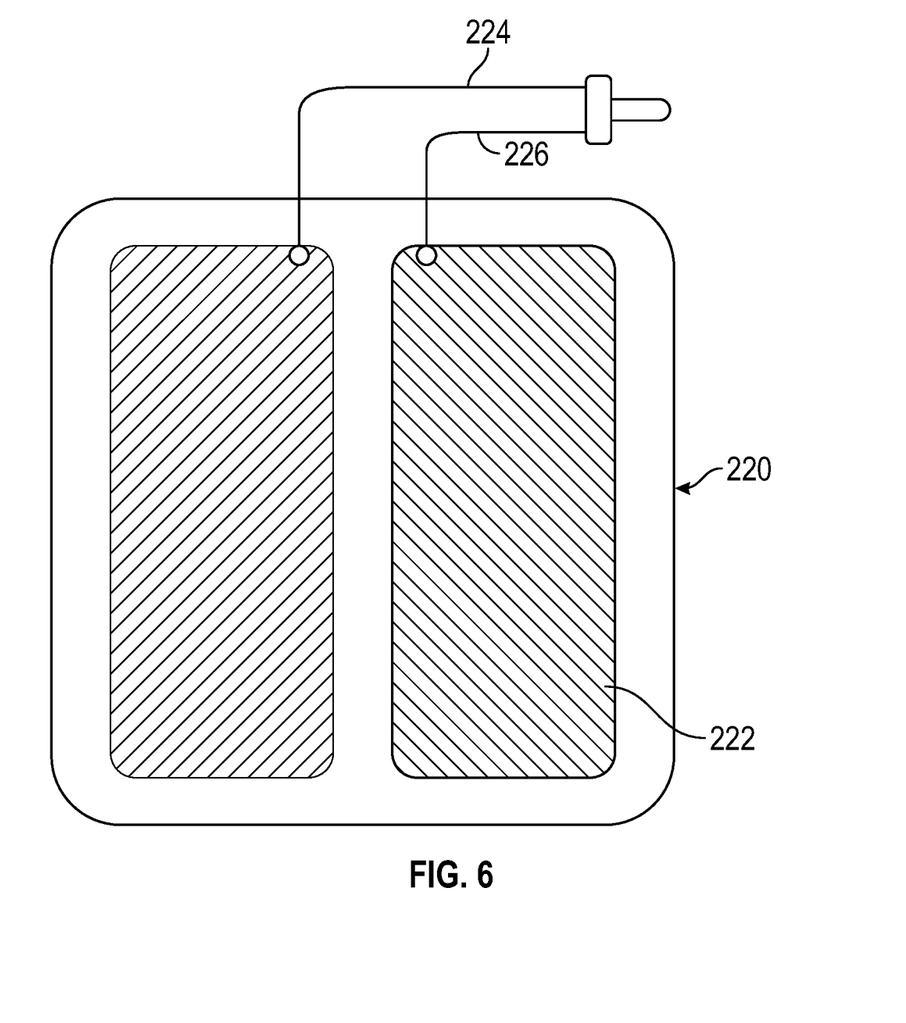
FIG. 6 is a bottom view of a return electrode of the patient return pad of FIG. 4.

With reference to FIGS. 4-6, another embodiment of a combination patient return pad and smoke evacuator 200 is illustrated and generally includes a head, such as, for example, a housing 204, a return electrode 220 attached to the housing 204, and a suction tube, such as, for example, the suction tube 106 (FIG. 2) supported by the housing 204. The housing 204 may have a box-shape or any other suitable shape and has an opened front end 204a and a closed rear end 204b. In aspects, the front end 204a may be planar (FIG. 4) or have a curved or scooped configuration (FIG. 5) to better allow for the front end 204a to surround a surgical opening.

A vacuum pathway is defined between the front 204a and rear ends 204b of the housing 204 and extends in the direction toward the rear end 204b. The housing 204 has a top surface 208a, a bottom surface 208b configured to face a tissue surface of a patient, and a pair of side walls 208c, 208d. The housing 204 may include a pad 216, such as, for example, a foam pad, received in a cavity 214 (FIG. 5) defined by the housing 204 to prevent debris from entering the cavity 214. The housing 204 has a vacuum connector 216 coupled to the top surface 208a and in fluid communication with the cavity 214. The suction tube 106 (FIG. 2) is configured to couple to the vacuum connector 218 to fluidly communicate with the opened front end 204a of the housing 204.

The return electrode 220 may be a split return electrode pad and is attached to the bottom surface 208b of the housing 204. The return electrode 220 may be a sheet, a wire, or a coating and may be made from materials that include aluminum, copper, mylar, metalized mylar or other suitable conductive material. The return electrode 220 has a bottom surface 222 having coated thereon an electrically-conductive adhesive (e.g., a conductive adhesive hydrogel) or other material that is configured to attach the return electrode 220 to tissue. A backing (not explicitly shown) may be provided that covers the bottom surface 222 of the return electrode 220. The backing may be selectively removed (e.g., peeled) from the bottom surface 222 to expose the adhesive.

The return electrode 222 has a pair of return leads 224, 226 extending therefrom. In particular, the return leads 224, 226, which may be wires or cables, have a first end portion attached to the return electrode 220, and a second end portion attached to the electrosurgical generator 12 (FIG. 1). The return leads 224, 226 transfer electrosurgical energy received by the return electrode 220 to the electrosurgical generator 12. In aspects, only one return lead may be provided.

Figure 7:
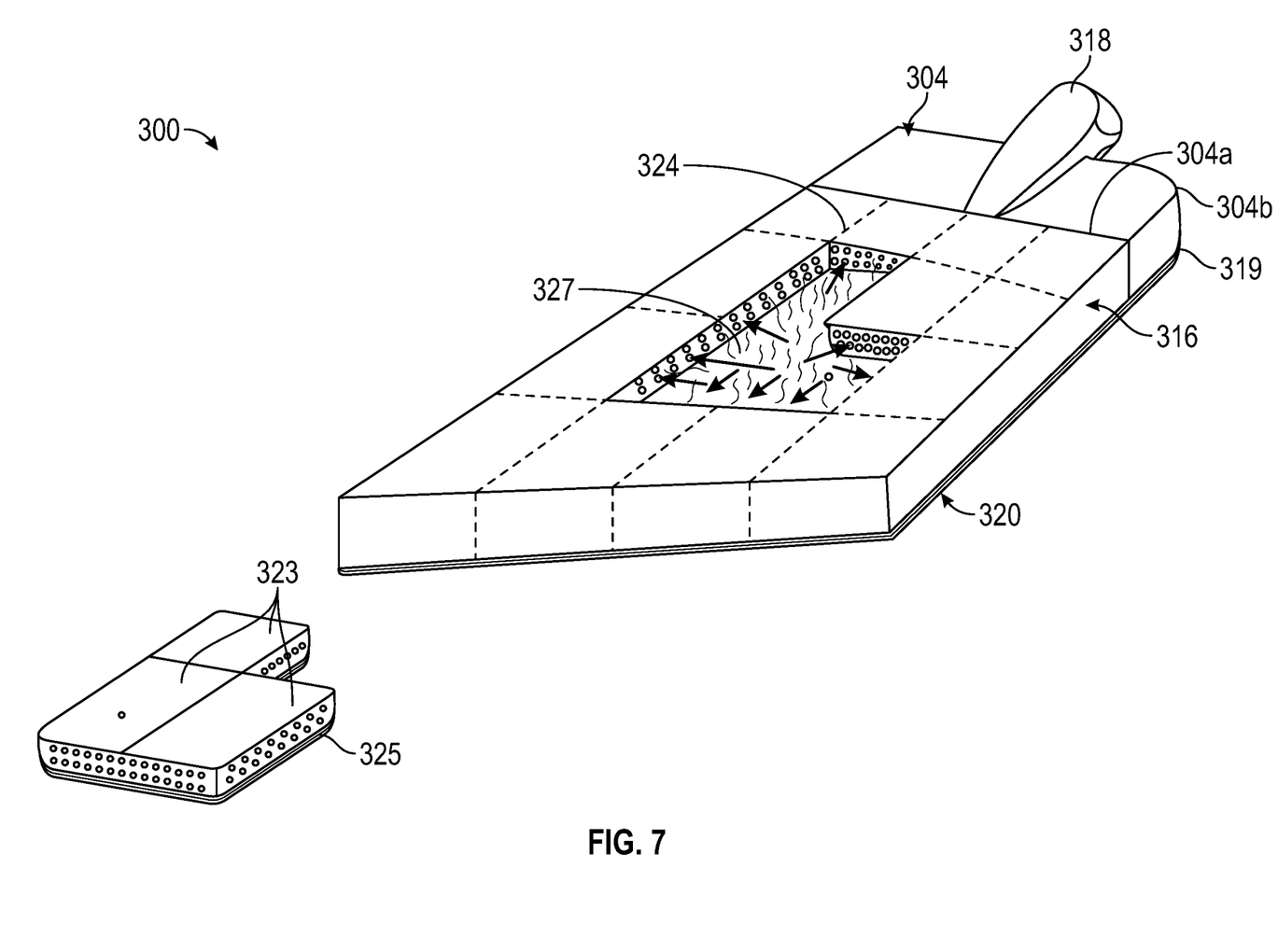
FIG. 7 is a perspective view of yet another embodiment of a patient return pad for use in the monopolar electrosurgical system.

With reference to FIG. 7, yet another embodiment of a combination return pad and smoke evacuator 300 is illustrated and generally includes a head, such as, for example, a housing 304, a return electrode 320 attached to the housing 304, a suction tube, such as, for example, the suction tube 106 (FIG. 2) supported by the housing 304, and a perforated foam pad 316 supported on the return electrode 320. The housing 304 has an opened front end portion 304a and a closed rear end portion 304b. The housing 304 defines a cavity (not explicitly shown) therein configured to be in communication with the suction tube 106 (FIG. 2) via a vacuum connector 318. In aspects, the vacuum connector 318 may be directly attached to the foam pad 316. In aspects, the housing 304 may cover an upper surface and lateral sides of the foam pad 316.

The return electrode 320 may be a flat sheet of material covering a bottom surface 319 of the housing 304 and extending distally from the front end portion 304a. The foam pad 316 is supported on the return electrode 320 and covers the opened front end portion 304a of the housing 304. The foam pad 316 has a plurality of perforations 324 defining a plurality of removable sections 323 to allow for the customization of the foam pad 316. The removable sections 323 may include a corresponding section 325 of the return electrode 320, such that upon removing the removable sections 323, an opening 327 may be formed in the smoke evacuator 300. The opening 327 may be positioned over a surgical site or access opening to surround the outer periphery of the access opening with the smoke evacuator 300.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure.

What is claimed is:

1. A combination patient return pad and surgical smoke evacuator, comprising:
    a housing defining a cavity therein configured to receive suction;
    a return electrode directly coupled to a surface of the housing and including an adhesive material configured to attach the return electrode to tissue, the return electrode configured to return energy, applied to the tissue by an energy source through an active electrode, back to the energy source; and
    a suction tube having a first end portion configured to be coupled to a vacuum source, and a second end portion configured to be coupled to the housing to be in fluid communication with the cavity for vacuuming surgical smoke through the cavity.

2. The combination patient return pad and surgical smoke evacuator according to claim 1, wherein the housing includes a bottom surface, the return electrode being directly coupled to the bottom surface of the housing.

3. The combination patient return pad and surgical smoke evacuator according to claim 1, wherein the return electrode includes a bottom surface configured to receive the energy from the active electrode.

4. The combination patient return pad and surgical smoke evacuator according to claim 3, wherein the bottom surface of the return electrode is directly coupled to a bottom surface of the housing.

5. The combination patient return pad and surgical smoke evacuator according to claim 1, further comprising a foam pad received in the cavity.

6. The combination patient return pad and surgical smoke evacuator according to claim 1, wherein the housing has an opened front end and a rear end, the housing defining a vacuum path from the front end toward the rear end.

7. The combination patient return pad and surgical smoke evacuator according to claim 1, further comprising a return lead having a first end portion coupled to the return electrode, and a second end portion configured to electrically couple the return electrode to the energy source.

8. A combination patient return pad and surgical smoke evacuator, comprising:
    a housing defining a cavity therein configured to receive suction, the housing including an opened front end in fluid communication with the cavity;
    a return electrode directly coupled to a surface of the housing, the return electrode configured to return energy, applied to tissue by an energy source through an active electrode, back to the energy source; and
    a perforated foam pad supported on the return electrode and covering the opened front end of the housing.

9. The combination patient return pad and surgical smoke evacuator according to claim 8, wherein the return electrode covers a bottom surface of the housing and extends distally from the opened front end of the housing.

10. The combination patient return pad and surgical smoke evacuator according to claim 8, wherein the foam pad includes a plurality of removable sections.

11. The combination patient return pad and surgical smoke evacuator according to claim 8, wherein the housing has a vacuum connector in fluid communication with the cavity, the vacuum connector being configured to couple to a suction tube.

12. The combination patient return pad and surgical smoke evacuator according to claim 8, further comprising a suction tube having a first end portion configured to be coupled to a vacuum source, and a second end portion configured to be coupled to the housing to be in fluid communication with the cavity for vacuuming surgical smoke through the cavity.

13. The combination patient return pad and surgical smoke evacuator according to claim 8, wherein the housing includes a bottom surface, the return electrode being directly coupled to the bottom surface of the housing.

14. The combination patient return pad and surgical smoke evacuator according to claim 8, wherein the return electrode includes a bottom surface configured to receive the energy from the active electrode.

15. The combination patient return pad and surgical smoke evacuator according to claim 14, wherein the bottom surface of the return electrode is directly coupled to a bottom surface of the housing.

16. The combination patient return pad and surgical smoke evacuator according to claim 15, wherein the bottom surface of the return electrode has an adherent portion and a conductive portion.

17. The combination patient return pad and surgical smoke evacuator according to claim 8, wherein the housing includes a rear end, the housing defining a vacuum path from the opened front end toward the rear end.

18. The combination patient return pad and surgical smoke evacuator according to claim 8, further comprising a return lead having a first end portion coupled to the return electrode, and a second end portion configured to electrically couple the return electrode to the energy source.

19. A combination patient return pad and surgical smoke evacuator, comprising:
    a housing defining a cavity therein configured to receive suction, the housing including an opened front end in fluid communication with the cavity;
    a return electrode coupled to the housing and including a removable portion positioned at a central region of the return electrode, the return electrode configured to return energy, applied to tissue by an energy source through an active electrode, back to the energy source; and
    a perforated foam pad supported on the return electrode and covering the opened front end of the housing, the foam pad including a plurality of removable sections,
    wherein upon removal of the removable portion of the return electrode and at least one removable section of the plurality of removable sections of the foam pad that is supported on the removable portion of the return electrode, a central opening is formed through the foam pad and the return electrode.

* * * * *